United States Patent
Hassler et al.

(10) Patent No.: US 9,917,654 B2
(45) Date of Patent: Mar. 13, 2018

(54) CHIP FOR TRANSDERMAL EMISSION OR AUGMENTATION OF ENERGY

(71) Applicants: Richard Michael Hassler, Laconia, NH (US); Michael Gerhard Hassler, Laconia, NH (US)

(72) Inventors: Richard Michael Hassler, Laconia, NH (US); Michael Gerhard Hassler, Laconia, NH (US)

(*) Notice: Subject to any disclaimer, the term of this patent is extended or adjusted under 35 U.S.C. 154(b) by 301 days.

(21) Appl. No.: 14/670,152

(22) Filed: Mar. 26, 2015

(65) Prior Publication Data

US 2016/0285565 A1 Sep. 29, 2016

Related U.S. Application Data

(60) Provisional application No. 62/062,485, filed on Oct. 10, 2014.

(51) Int. Cl.
*A61N 1/40* (2006.01)
*H04B 13/00* (2006.01)
*H04B 5/00* (2006.01)
*A61N 5/06* (2006.01)
*G03H 1/00* (2006.01)

(52) U.S. Cl.
CPC ......... *H04B 13/005* (2013.01); *H04B 5/0093* (2013.01); *A61N 5/062* (2013.01); *G03H 1/0005* (2013.01)

(58) Field of Classification Search
CPC .................. A61N 5/062; A61H 2201/10
See application file for complete search history.

(56) References Cited

U.S. PATENT DOCUMENTS

| | | |
|---|---|---|
| 2003/0133596 A1 | 7/2003 | Brooks |
| 2005/0046573 A1 | 3/2005 | Velasco et al. |
| 2007/0195548 A1* | 8/2007 | Wang ............... A61N 5/062 362/555 |
| 2008/0308541 A1 | 12/2008 | Finn |
| 2012/0130362 A1 | 5/2012 | Hastings et al. |
| 2012/0226095 A1 | 9/2012 | Young |

* cited by examiner

*Primary Examiner* — Michael D Abreu
(74) *Attorney, Agent, or Firm* — Mark H. Plager

(57) ABSTRACT

A hologram chip may be programmed to emit and/or augment energy tuned to interact with bodily functions through transdermal contact. The chip may be programmed by using a pair of Tesla pancake coils, each coupled to a spherical electrode and driven to create an energetic field between the electrodes. The hologram chip may be in contact with a transmitter coil. A tuning medium may be in contact with a receiver coil. A wave function generator may drive the transmitter coil until it is in resonance with the receiver coil causing an energetic field to form between the spherical electrodes. The longitudinal waves passed from the transmitter side to the receiver side may be conducted through the receiver pancake coil and through the tuning medium, which in turn may transmit the natural frequencies/information of the tuning medium through the longitudinal waves to the hologram chip on the transmitter coil.

2 Claims, 3 Drawing Sheets

CHIP FOR TRANSDERMAL EMISSION OR AUGMENTATION OF ENERGY

CROSS-REFERENCE TO RELATED APPLICATIONS

This application claims benefit under 35 U.S.C. § 119(e) of U.S. Provisional Application having Ser. No. 62/062,485 filed Oct. 10, 2014, which is hereby incorporated by reference herein in its entirety.

BACKGROUND

The embodiments herein relate generally to chips for transdermal emission/augmentation of energy.

The ability to carry information through longitudinal wave carriers has until now, been underutilized. FIG. 1 shows an example of a Tesla coil, waveform/signal generator connected to a spherical electrode as disclosed by Konstantin Meyl's book *Scalar Wave Technology: Documentation for the Experimental-Kit for the Transmission of Electrical Scalar Waves*. Configured correctly, the Tesla coil may produce a longitudinal wave which may carry energetic information over space. FIG. 2 shows a configuration of connections of the components of longitudinal (scalar) electromagnetic wave/field generating equipment with additional connections to different jumper fields as disclosed by Konstantin Meyl. The configuration may transfer a waveform signal from the transmitter side to the receiver side and vice versa via the longitudinal waves carried through the field between two spherical electrodes.

SUMMARY

According to one embodiment of the subject technology, a chip for transdermal emission/augmentation of energy comprises a chip body, a holographic layer of the chip body, and a hologram in the holographic layer. The hologram may emit and/or augment energetic frequencies/information tuned via longitudinal carrier waves from a pair of pancake coils passed through a tuning medium. The energetic frequencies/information of the hologram may be tuned for interaction with a bodily function.

According to another embodiment of the subject technology, a system for programming chips for transdermal emission/augmentation of energy comprises a wave function generator, a transmitter pancake coil, a first spherical electrode electrically coupled to the transmitter pancake coil, a hologram chip in proximity to the transmitter pancake coil, a receiver pancake coil electrically coupled to the transmitter pancake coil, a second spherical electrode electrically coupled to the receiver pancake coil, and a tuning medium in proximity with the receiver pancake coil. The tuning medium may include natural frequencies/information that is transferred to the hologram chip in response to a wave function driving the transmitter pancake coil. The driven transmitting pancake coil may cause an energetic field between the first and second spherical electrodes to charge the receiver pancake coil and transmit the natural frequencies/information of the tuning medium to the hologram chip.

According to yet another embodiment of the subject technology, a method of programming a hologram chip for use in transdermal emission/augmentation of energy, comprises positioning the hologram chip in proximity to a transmitter pancake coil and positioning a tuning medium in proximity to a receiver pancake coil. The transmitter pancake coil is electrically coupled to a first spherical electrode, the receiver pancake coil is electrically coupled to a second spherical electrode, and the transmitter pancake coil is electrically coupled to the receiver pancake coil. The method further comprises driving a wave generator to provide a driving frequency to the transmitter pancake coil to produce an energetic field between the first and second spherical electrodes, the energetic field driving the receiver pancake coil to transmit the frequencies/information of the tuning medium to the transmitter pancake coil to charge the hologram chip with the frequencies/information of the tuning medium.

BRIEF DESCRIPTION OF THE FIGURES

The detailed description of some embodiments of the present invention is made below with reference to the accompanying figures, wherein like numerals represent corresponding parts of the figures.

DETAILED DESCRIPTION OF CERTAIN EMBODIMENTS

Broadly, embodiments of the subject technology provide a system, method, and product of the system and method that uses information carried by longitudinal waves to program a chip for transdermal emission and/or augmentation of energy. In an exemplary use, the chip may be integrated into a wearable article or directly worn by a person. The chip may be programmed to emit and/or augment energetic frequencies/information that are tuned to interact with a bodily function. In an exemplary embodiment, the chip includes a hologram carrying the information. For example, the hologram may be tuned to output and/or augment an energetic frequency that causes blood flow to increase/decrease within a portion of the body in proximity to the chip.

The word "exemplary" is used herein to mean "serving as an example or illustration." Any aspect or design described herein as "exemplary" is not necessarily to be construed as preferred or advantageous over other aspects or designs. The word "information" is used herein to refer to a specific frequency or range of frequencies emitted by an object in the form of a longitudinal (scalar) wave or field. The word "augment" is used herein to refer to interacting with the charge or field of another object.

Figure 1:
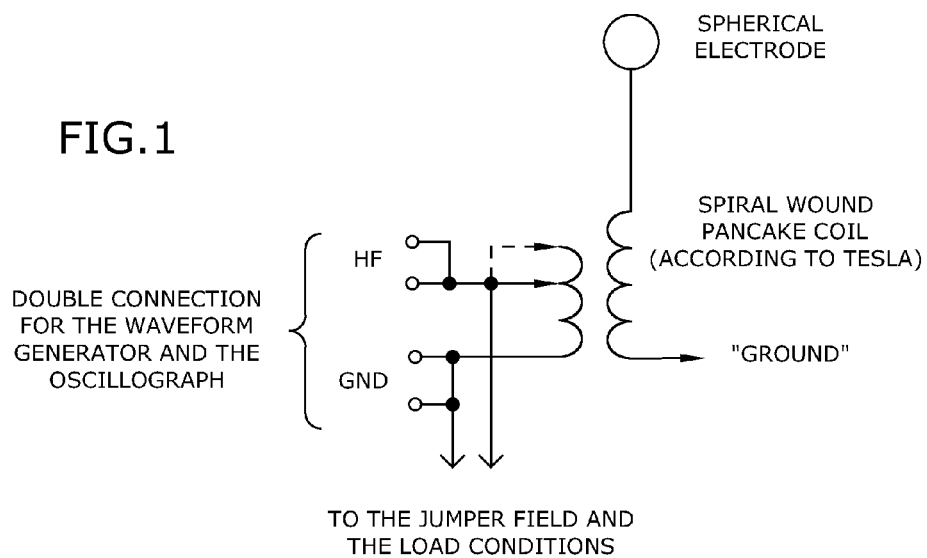
FIG. 1 is a schematic of an air cored transformer with couple coil and pancake coil.
Figure 3:
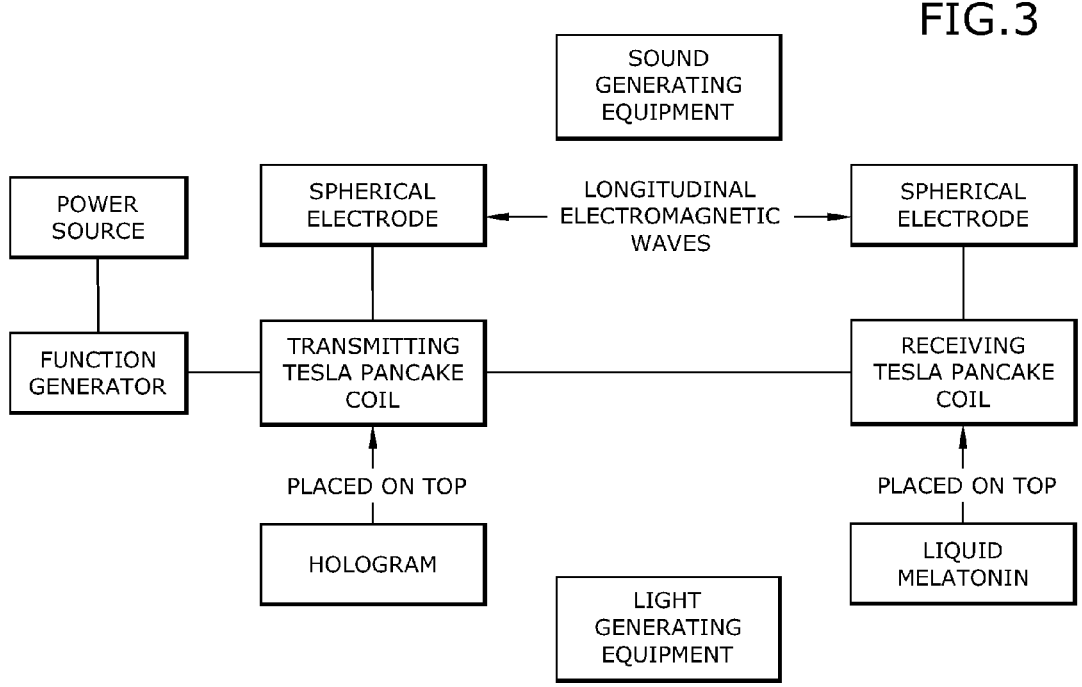
FIG. 3 is a block diagram of a system for programming a chip for transdermal emission of energy in accordance with an embodiment of the subject technology.
Figure 2:
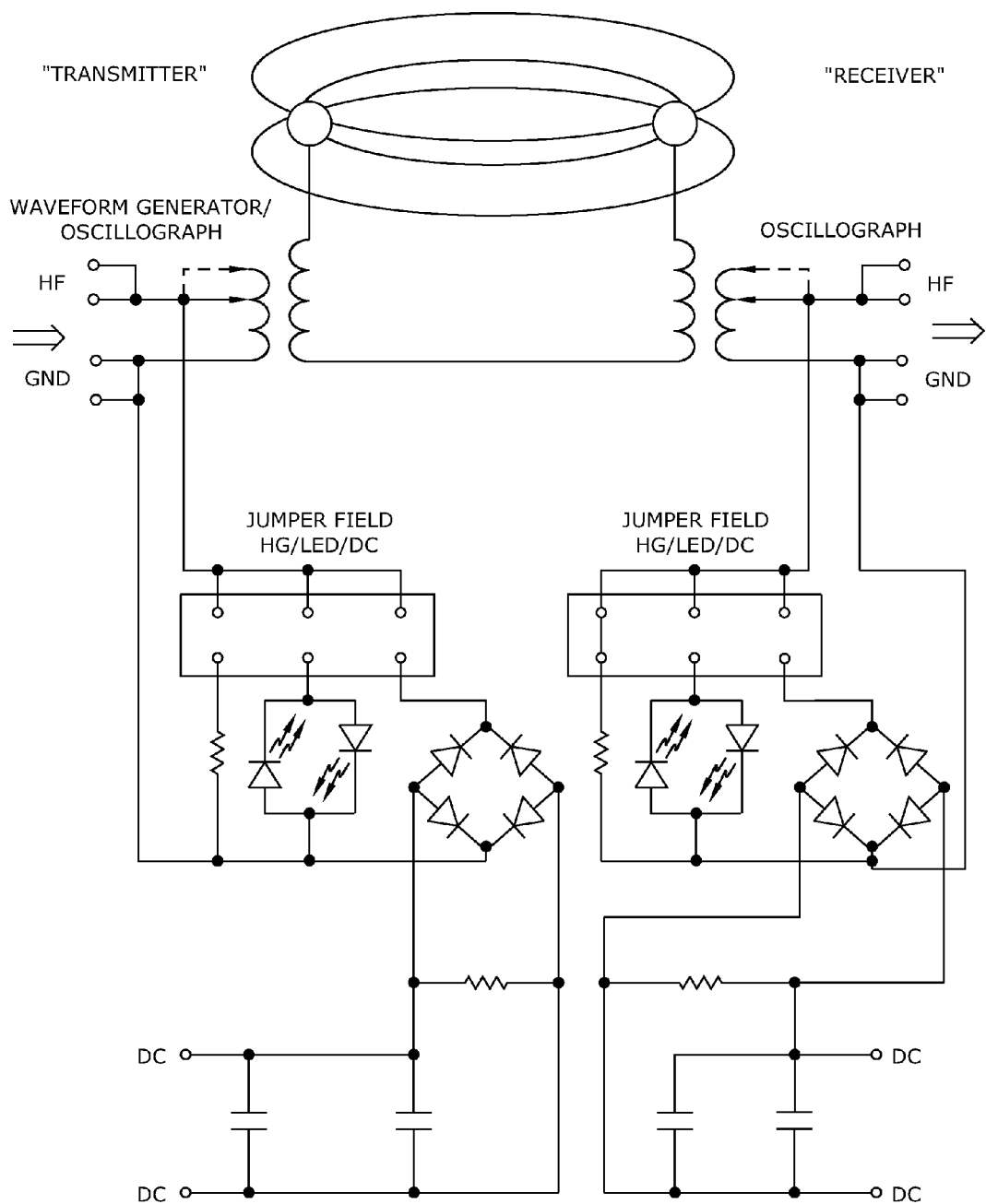
FIG. 2 is a schematic of a longitudinal wave/field generating circuit.
Figure 4:
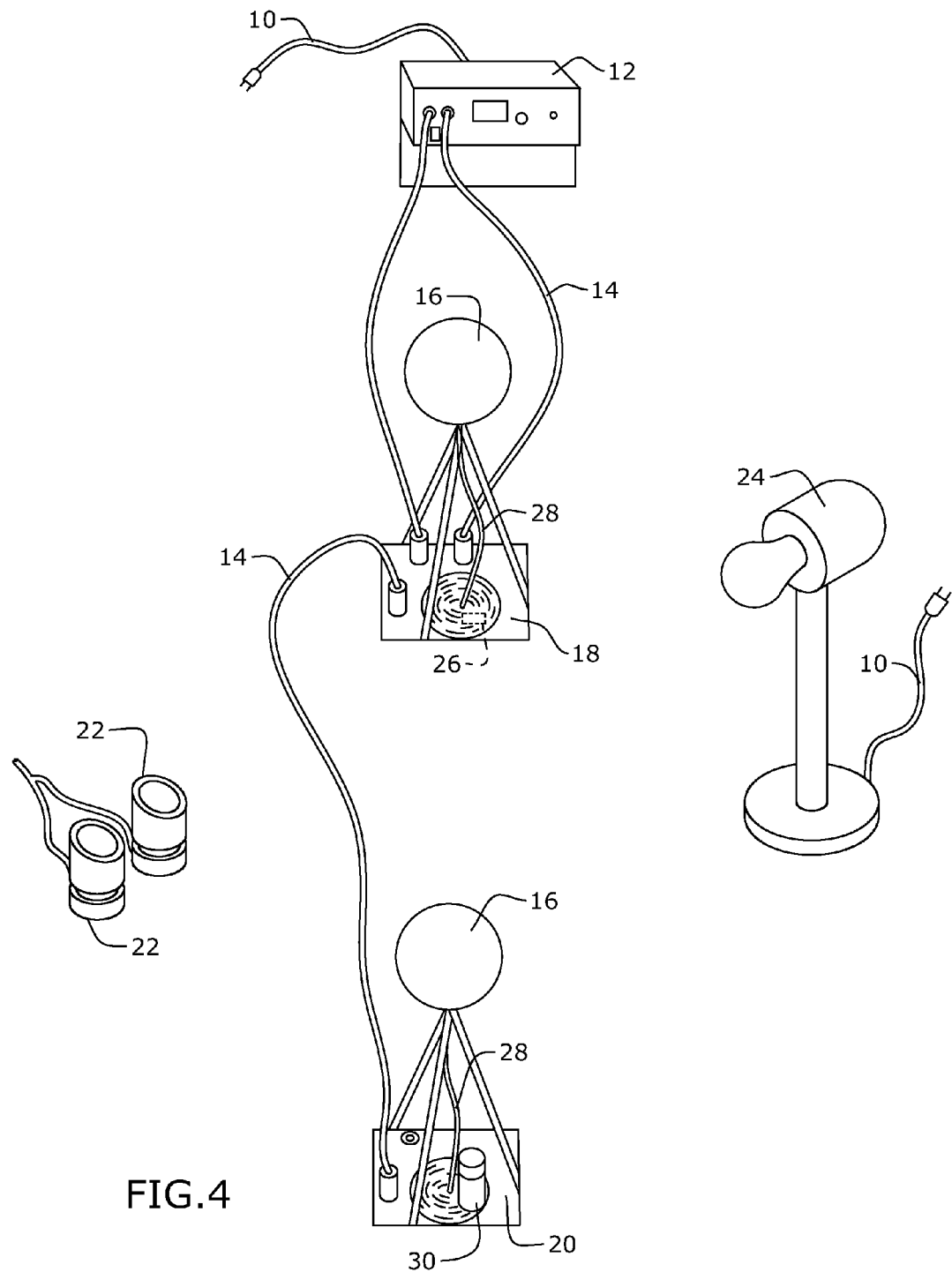
FIG. 4 is a perspective view of a system setup for programming a chip for transdermal emission of energy in accordance with an embodiment of the subject technology.

Referring now to FIGS. 3 and 4, an exemplary a system setup for programming a hologram chip according to an exemplary embodiment of the subject technology is shown. In general, a transmitting pancake coil 18 (sometimes referred to as a Tesla coil) is electrically connected to a receiver pancake coil 20. The transmitting pancake coil 18 and receiver pancake coil 20 may be separated by a predetermined distance (for example, 3 feet) and each may be connected to a respective spherical electrode 16 separated by approximately the same distance. A programmable object 26, for example, a hologram chip may be positioned in proximity to (or in contact with) the transmitting pancake coil 18. It will be understood that the proximity to the transmitting pancake coil 18 may be based on the magnitude of the field generated by the coil 18. The programmable object 26 may be any object that can carry a longitudinal (scalar) charge or a longitudinal (scalar) wave field. For sake of illustration, the programmable object 26 will be referred to herein as the hologram chip 26. The hologram chip 26 may include a chip body with a holographic layer containing a hologram. The hologram may emit and/or augment energetic frequencies/information through transdermal means. The hologram may be programmed to the natural frequencies/information of a tuning medium 30 positioned in contact with the receiver pancake coil 20. The tuning medium 30 may be any crystalline structure or liquid. In the example shown, liquid melatonin is a tuning medium 30 whose natural frequencies/information may be programmed into the hologram so that the frequencies/information may be turned into an energetic signal which can be transmitted transdermally from the chip to the user. The information carried by the natural frequencies/information of melatonin may thus interact with a portion of the body affecting certain functions.

To tune the hologram chip 26, an exemplary method generates and augments longitudinal waves/field to carry the information from the tuning medium 30 to the hologram chip 26. A power source 10 may power a wave function generator 12 (for example a direct digital synthesis function generator) to produce wave signals. The wave function generator 12 may be tuned so the waves are in resonance. This can be achieved with a sine wave at an output amplitude of approximately 8 $V_{PP}$ (Volts peak to peak) and a frequency of around 6 MHz (megahertz). Longitudinal waves may be produced in a field between the spherical electrodes 16. Energy from the receiving side spherical electrode 16 passing through the tuning medium 30 on the receiver pancake coil 20 may modulate the carrier longitudinal waves/fields to transfer the natural frequencies/information of the tuning medium 30 to the wave signals once the waves become in resonance. As shown, wiring 14 may electrically couple the power source 10 to the wave function generator 12, the wave function generator 12 to the transmitter pancake coil 18, and the transmitter pancake coil 18 to the receiver pancake coil 20.

In some embodiments, a sound source 22 and light source 24 may be included to augment/modulate the carrier longitudinal waves. In an exemplary embodiment, the sound source 22 may produce sound waves at variable frequencies. The sound source 22 may be positioned approximately three feet perpendicular to the middle of the line created by the transmitter pancake coil 18 and receiver pancake coil 20. The light source 24 may produce light waves at variable frequencies on the opposite side of the sound source 22. The light source 24 may be positioned approximately three feet perpendicular to the middle of the line created by the transmitter pancake coil 18 and receiver pancake coil 20. The sound source 22 may be tuned to a frequency of approximately 20 Hertz. The light source 24 may be tuned to a frequency of approximately 20 Hertz. The sound and light waves produced may augment/modulate the carrier longitudinal (scalar) waves/fields to transfer additional specific information and/or messages. The light and sound waves directly affect the longitudinal waves by influencing both the longitudinal waves/field as well as the receiving/transmitting coils. The light and sound do not necessarily change the information the melatonin is sending to the hologram chip 26 but may only adds to information associated with the melatonin If the frequencies for melatonin (or another tuning medium 30) were known then they can be played through the speakers and light to add more information into the hologram chip 26. In an exemplary embodiment, the system may run for approximately thirty minutes for the hologram to be transformed with the information transferred by the longitudinal waves.

Persons of ordinary skill in the art may appreciate that numerous design configurations may be possible to enjoy the functional benefits of the inventive systems. Thus, given the wide variety of configurations and arrangements of embodiments of the present invention the scope of the present invention is reflected by the breadth of the claims below rather than narrowed by the embodiments described above.

What is claimed is:

1. A method of programming a hologram chip or substrate for use in transdermal applications, comprising:
    positioning the hologram chip in proximity to a transmitter pancake coil;
    positioning a tuning medium in proximity to a receiver pancake coil, wherein the transmitter pancake coil is electrically coupled to a first electrode, the receiver pancake coil is electrically coupled to a second electrode, and the transmitter pancake coil is electrically coupled to the receiver pancake coil; and
    driving wave function generator at a resonance frequency producing longitudinal electromagnetic scalar waves in an area between and proximate the first and second electrodes;
    modulating the longitudinal electromagnetic scalar wave with energy passed through a substance in the tuning medium, a wave or field source of light and/or sound operated at a predetermined frequency having an amplitude of a waveform change to modulate desired information onto a carrier wave directed at the longitudinal electromagnetic scalar wave;
    conducting the modulated longitudinal electromagnetic scalar wave to the receiver pancake coil; and
    embedding the hologram or substrate with the desired information in the form of the modulated longitudinal electromagnetic scalar wave programmed by the predetermined frequency of the wave or field source and the signal wave from the wave function generator, wherein the hologram chip is used for transdermal emission when worn by a user.

2. The method of claim 1, further comprising modulating the energetic field with a second wave modulation source.

* * * * *